(12) United States Patent
Emigh

(10) Patent No.: US 9,393,460 B1
(45) Date of Patent: Jul. 19, 2016

(54) INTELLIGENT PERSONAL FITNESS DEVICE

(71) Applicant: Aaron Emigh, Incline Village, NV (US)

(72) Inventor: Aaron Emigh, Incline Village, NV (US)

( * ) Notice: Subject to any disclaimer, the term of this patent is extended or adjusted under 35 U.S.C. 154(b) by 114 days.

(21) Appl. No.: 14/147,477

(22) Filed: Jan. 3, 2014

Related U.S. Application Data

(60) Provisional application No. 61/748,733, filed on Jan. 3, 2013, provisional application No. 61/748,734, filed on Jan. 3, 2013, provisional application No. 61/748,735, filed on Jan. 3, 2013, provisional application No. 61/769,205, filed on Feb. 26, 2013, provisional application No. 61/769,206, filed on Feb. 26, 2013, provisional application No. 61/769,207, filed on Feb. 26, 2013, provisional application No. 61/769,208, filed on Feb. 26, 2013.

(51) Int. Cl.
*A63B 69/00* (2006.01)
*A63B 24/00* (2006.01)

(52) U.S. Cl.
CPC ......... *A63B 24/0062* (2013.01); *A63B 2220/17* (2013.01); *A63B 2225/20* (2013.01)

(58) Field of Classification Search
CPC ........... A63B 2220/17; A63B 2225/20; A63B 24/0075
See application file for complete search history.

(56) References Cited

U.S. PATENT DOCUMENTS

| | | | | |
|---|---|---|---|---|
| 2008/0090703 A1* | 4/2008 | Rosenberg | ......................... | 482/8 |
| 2013/0267287 A1* | 10/2013 | Goldenberg | .................... | 463/10 |

* cited by examiner

*Primary Examiner* — Omeed Alizada

(57) ABSTRACT

In some embodiments, techniques for a intelligent personal fitness device include determining an exercise equipment; determining an exercise associated with the exercise equipment; determining a parameter associated with the exercise equipment; detecting a number of repetitions of the exercise associated with the exercise equipment performed using the exercise equipment, wherein detecting the number of repetitions of the exercise associated with the exercise includes analyzing data from an accelerometer; calculating an activity score based at least in part on the exercise associated with the exercise equipment, the parameter associated with the exercise equipment, and the number of repetitions of the exercise; and providing the activity score.

19 Claims, 3 Drawing Sheets

INTELLIGENT PERSONAL FITNESS DEVICE

CROSS REFERENCE TO RELATED APPLICATIONS

This application claims priority to U.S. Provisional Patent Application No. 61/748,733, entitled NUTRITIONAL TRACKING, filed Jan. 3, 2013, which is incorporated herein by reference for all purposes, and to U.S. Provisional Patent Application No. 61/748,734, entitled PERSONAL FITNESS DEVICE WITH INTERCOMMUNICATING EXERCISE EQUIPMENT, filed Jan. 3, 2013, which is incorporated herein by reference for all purposes, and to U.S. Provisional Patent Application No. 61/748,735, entitled PERSONAL FITNESS DEVICE WITH HISTORICALLY-BASED EXERCISE INFERENCE, filed Jan. 3, 2013, which is incorporated herein by reference for all purposes, and to U.S. Provisional Patent Application No. 61/769,205, entitled PERSONAL FITNESS DEVICE WITH MOVEMENT-BASED EXERCISE INFERENCE, filed Feb. 26, 2013, which is incorporated herein by reference for all purposes, and to U.S. Provisional Patent Application No. 61/769,206, entitled PERSONAL FITNESS DEVICE WITH EXERCISE EQUIPMENT IDENTIFICATION, filed Feb. 26, 2013, which is incorporated herein by reference for all purposes, and to U.S. Provisional Patent Application No. 61/769,207, entitled PERSONAL FITNESS DEVICE WITH LOCATION-BASED EXERCISE INFERENCE, filed Feb. 26, 2013, which is incorporated herein by reference for all purposes, and to U.S. Provisional Patent Application No. 61/769,208, entitled PERSONAL FITNESS DEVICE WITH TRANSMISSION OF SETTINGS, filed Feb. 26, 2013, which is incorporated herein by reference for all purposes.

FIELD OF THE INVENTION

The present invention relates generally to the area of personal fitness. More specifically, techniques for intelligent operation of personal fitness devices are disclosed.

BACKGROUND OF THE INVENTION

Personal fitness devices that purport to track physical activity are a burgeoning new product category. However, such devices, are presently unable to detect what type of activity a motion represents. Because similar motions can represent very different levels and types of exercise (consider the difference between moving one's arms in front of one's body, and bench pressing hundreds of pounds), this represents a very significant limitation.

Accordingly, it would be useful to have better ways to determine and track physical activity using a personal fitness device. It would also be useful to be able to transmit exercise parameters from a personal fitness device to an exercise machine, rendering the process less cumbersome and error-prone.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process, an apparatus, a system, a composition of matter, a computer readable medium such as a non-transitory computer readable storage medium (such as a magnetic storage medium, e.g. a disk, an electronic storage medium, e.g. a flash memory, or an optical storage medium, e.g. a CD-ROM or DVD-ROM) or a computer network wherein program instructions are sent over optical or electronic communication links. In this specification, these implementations, or any other form that the invention may take, may be referred to as techniques. In general, the order of the steps of disclosed processes may be altered within the scope of the invention.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
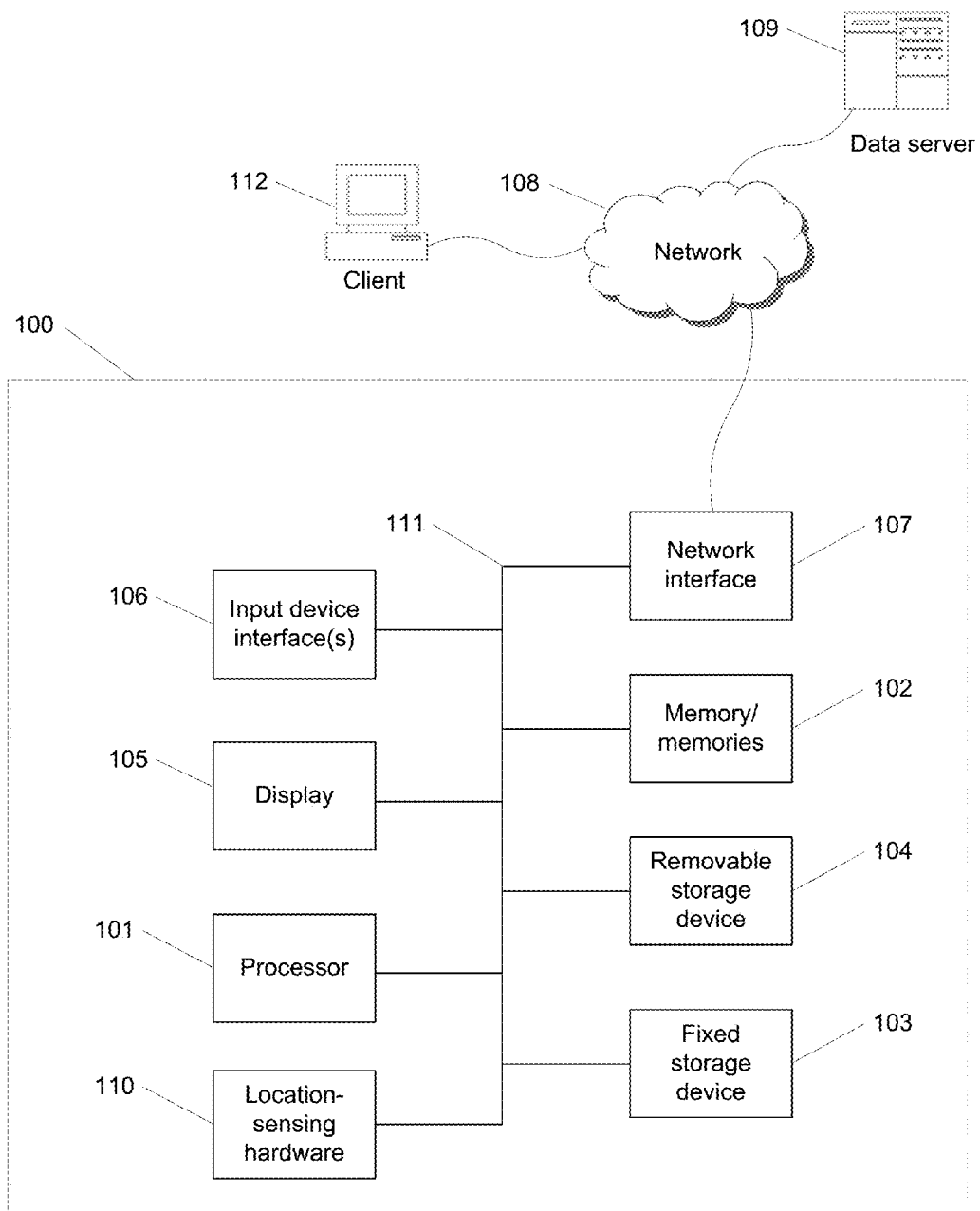
FIG. 1 is a diagram of a system for personal fitness device operation, according to some embodiments.

FIG. 1 is a diagram of a system for personal fitness device operation, according to some embodiments. As will be apparent, other computer system architectures and configurations can be used. In this example, computing device 100, which may be any computing device that can perform the techniques described herein, such as a wearable computer embedded in a bracelet, watch, anklet, smartphone, digital music player such as an MP3 player, pin, tab, clothing, glasses, etc., includes various subsystems as described below. It includes at least one microprocessor subsystem (also referred to as a processor or a central processing unit (CPU)) 101. In various embodiments, processor 101 may be implemented by a single-chip processor or by multiple processors. In some embodiments, processor 101 is a general purpose digital processor having one or more cores. Using instructions retrieved from one or more memories 102, processor 101 controls the reception and manipulation of input data, and the output and display of data on output devices (e.g., display 105). In some embodiments, processor 101 performs the client-side techniques described below in conjunction with the remaining Figures.

Processor 101 is coupled bi-directionally with a memory 102. Memory 102 may comprise multiple memories, and is referred to in the singular purely for expository simplicity. Memory 102 may include a first primary storage, typically a random access memory (RAM), and a second primary storage, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 101. Also as well known in the art, primary storage typically includes basic operating instructions, program code, data and objects used by the processor 101 to perform its functions (e.g., programmed instructions). In some embodiments, primary memory 102 may include any suitable computer-readable storage media, described below, depending on whether, for example, data access needs to be bidirectional or unidirectional. In some embodiments, processor 101 may also directly retrieve and store frequently needed data in one or more cache memories (not shown).

Fixed storage device 103 may provide data storage capacity for computing device 100, and is coupled either bidirectionally (read/write) or unidirectionally (read only) to processor 102. Examples of fixed storage device 103 include computer-readable media such as flash memory, a hard disk drive, an optical storage device such as a DVD-ROM, and other storage devices that retain their data when computing device 100 is powered off. Fixed storage device 103 may store additional programming instructions, data, and the like for processor 101, which may for example be loaded into memory 102 for use by processor 101 as needed. In some embodiments, a removable storage device 104, for example a flash memory card such as an SD card, a Micro SD card, or an SDHC card, provides additional data storage capacity. It will be appreciated that the information retained within storage devices 103, 104 can be incorporated, if needed, in standard fashion as part of memory 102 as virtual memory.

Display 105 may be any form of human-readable display, such as an LCD screen. Display 105 may display text and/or graphics as instructed by processor 101. In various embodiments, display 105 may be integrated with computing device 100, or may be separate and an interface between the two may be included in each respective component.

Input device interface(s) 106 provide interfaces, such as USB, through which user input may be received. Examples include a keyboard, a mouse, and a touchscreen.

Location sensing hardware 110 may be connected, directly or indirectly, to processor 101. Location sensing hardware 110 may be any hardware that can determine a current location of itself, and/or motions that are being experienced. Examples of location sensing hardware 110 include a GPS (Global Positioning System) satellite receiver, an accelerometer, a physical motion sensor such as a switch, micro switch, or magnetic reed switch, and/or a location receiving device such as a wirelessly networked device that receives information relating to a current location from transmitters, directly or indirectly.

Network interface 107 is hardware that provides access to network 108. In some embodiments, such as for wired networks, network interface 110 may include a plug, such as an Ethernet plug. In some embodiments, such as for wireless networks, network interface 107 may include an antenna.

Network 108 may be any type of network, for example a public network such as the internet or a cellular phone network such as a GPRS network. In another example, the network 108 may be an enterprise or home network, a virtual private network, or a wireless network such as an 802.11 or Bluetooth (including Bluetooth Low Energy) network. In another example, RFID reading via NFC (near field communications) may be a network 108. In some embodiments, the network 108 may include more than one network. An example of a network 108 including more than one network is a local area network connected to a public network such as the internet. An example of the use of such a network is for a computing device 100 to be connected via a local area network such as an enterprise network (for example via a wireless router), and for the local area network to be connected to data server 109 via a public network such as the internet.

Bus 111 may provide access between the various subsystems of computing device 100. Bus 111 is illustrative of any interconnection scheme serving to link the subsystems, including multiple independent and/or connected buses. Other computer architectures having different configurations of subsystems, and various other interconnection schemes, can also be utilized.

Other subsystems (not shown) may also be connected to bus 111, such as a digital camera, a microphone, and other subsystems known to those skilled in the art.

Data server 109 is connected, directly or indirectly, to the network 108. Data server 109 provides data to computing device 100 via network 108, for example by TCP/IP, HTTP, and/or proprietary protocols. In various embodiments, data server 109 (which in some embodiments may encompass several physical servers and/or services) may provide data relating to historical exercising, as well as other data as needed. Internally, data server 109 may be structured as discussed in conjunction with computing device 100, and in some embodiments, computing device 100 may be a data server 109.

Client 112 is connected, directly or indirectly, to the network 108. Client 112 may receive data from computing device 100 and/or data server 109 via network 108, for example by TCP/IP, HTTP, and/or proprietary protocols, and may present data to, and receive input from, one or more users. Internally, client 112 may be structured as discussed in conjunction with computing device 100, and in some embodiments, computing device 100 may be a client 112.

The techniques of the remaining figures can be run on one or more components of the system of this FIG. 1, as described above. In general, running techniques on this system comprises executing operations stored as numbers in memory 102 on processor 101, wherein the operations comprise computer-interpretable instructions for performing the techniques, by receiving data at processor 101 from memory 102, fixed storage device 103, and/or network interface 107, for example via bus 111, manipulating the data as specified, including using memory 102 for the inputs, intermediate values, and outputs needed for said manipulations, and using registers internal to processor 101, transmitting data to network interface 107, fixed storage device 103, and/or memory 102 (for example via bus 111), receiving inputs from input device interface 106 (for example via bus 111), and displaying results via display 105 (for example via bus 111). Such running may take place on computing device 100, data server 109 and/or client 112, and may take the form of direct execution of machine-readable code specifying operations to perform in order to perform the techniques, e.g. for machine code or code that has been compiled into machine code, or of the execution of an interpreter that interprets either source code specifying the techniques, or a compiled intermediate code (such as bytecode for a JVM) specifying the techniques, and performs the actions so specified.

Figure 2:
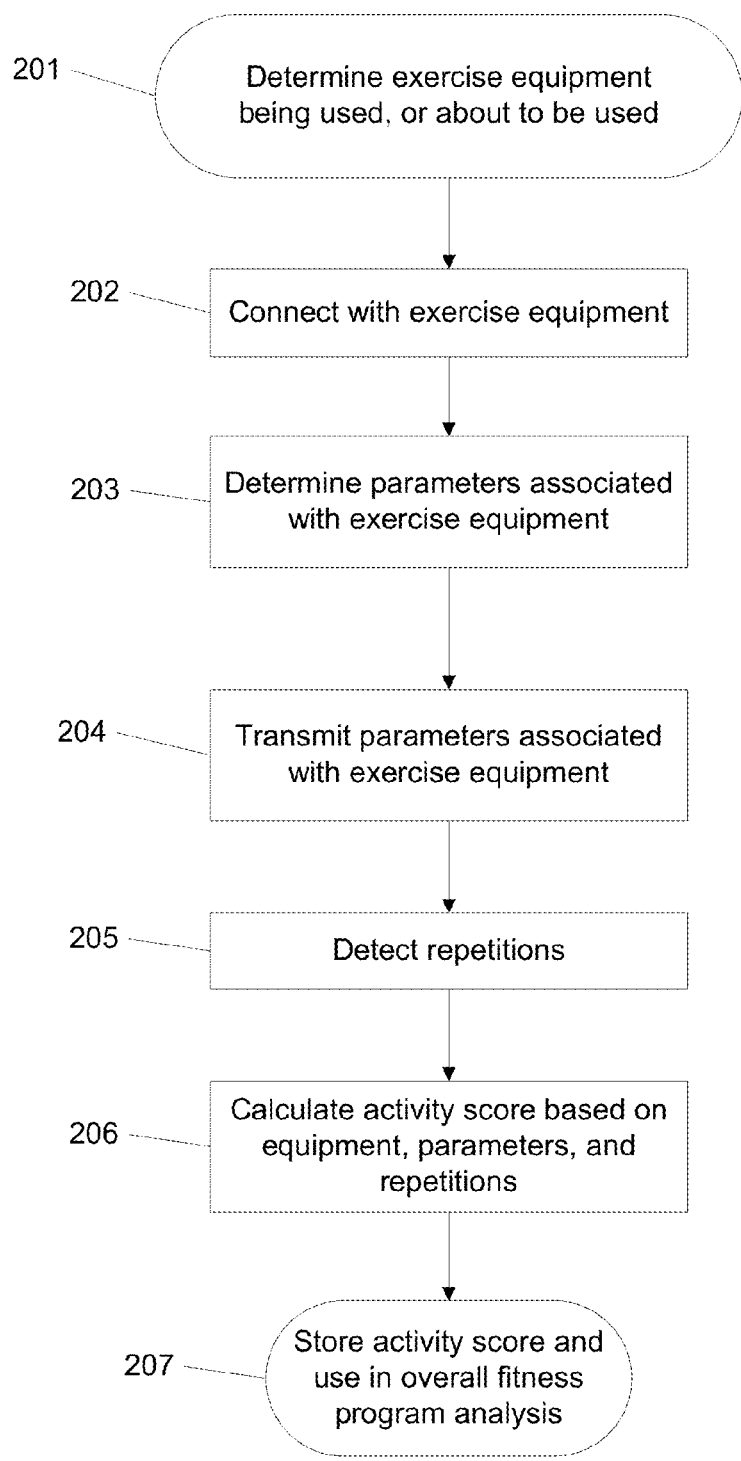
FIG. 2 is a flow diagram of a method for operating a personal fitness device, according to some embodiments.

FIG. 2 is a flow diagram of a method for operating a personal fitness device, according to some embodiments. In this example, a personal fitness device, hereinafter referred to as a PFD, refers to any portable device suitable for performing the techniques herein, for example a computing device 100 of FIG. 1, which may be a computing device such as a wearable computer embedded in a bracelet, watch, anklet, smartphone, digital music player such as an MP3 player, pin, tab, clothing, glasses, etc.

It may be determined what exercise equipment is being used, or about to be used (201). Exercise equipment refers herein to any equipment used for exercise and/or fitness, including cardio equipment such as exercise bikes, treadmills, and stairclimbing machines, weight equipment such as weight machines, free weights with associated barbells and/or dumbbells, integrated barbells and/or dumbbells, assisted or non-assisted body-weight machines such as pull-up and/or dip machines, TRX trainers, etc.

An example of determining what exercise equipment is being used is for the user to scan a barcode such as a QR code, using techniques well known to those skilled in the art, using a digital camera on a PFD or a smartphone coupled to the PFD via a wireless network such as Bluetooth. The resulting image may be analyzed and a code may be determined, which in various embodiments may correspond to an exercise equipment designation, or a URL with standard parameters which may be parsed and used, or from which data in a standard format such as XML, HTML, or JSON may be retrieved and used. Another example of such a determination is optical character recognition applied to an image that includes text, such as a placard describing the equipment. Another example of such a determination is to scan an RFID tag based using NFC, which may result in data that can be processed as described above. Another example of such a determination is object recognition via machine vision, which may infer which of a candidate set of previously seen equipment (or predetermined equipment) the imaged equipment most resembles, using techniques known to those skilled in the art, and either selecting such equipment automatically if the similarity exceeds a threshold, or allowing the user to select from among a candidate set of similar equipment, if the identification is ambiguous.

Another example of determining what exercise equipment is being used is to detect a broadcast from a wireless beacon, such as a Bluetooth (including Bluetooth Low Energy, hereinafter referred to as BTLE) beacon. Such a beacon may broadcast identifying information as described above for the exercise equipment. In some embodiments, it may be determined whether the power of the Bluetooth signal exceeds a threshold, and will be determined to be the equipment that is about to be used only if it exceeds the threshold. Such a threshold may be tuned to ensure that the PFD is within a threshold distance (such as 5-10 cm) from the exercise equipment, Bluetooth beacon, or RFID/NFC tag on/in the exercise machine, which in some embodiments may be labeled to aid the user in locating it, in order to determine the exercise equipment.

In some embodiments, it may be detected that the user has tapped the device on the exercise machine prior to detection (e.g. via Bluetooth or NFC, or by location, history, or motion analysis as discussed below). In some embodiments, the accelerometer may be used by the PFD for peering. For example, the user may tap the PFD on the machine, and software on the PFD may detect an especially sharp, transient spike in acceleration (slowing—deceleration), and may then either automatically peer with the highest-energy radio signal fitness machine available, or make it available for peering by the user (which may include an option to select other, lower-energy radio signal exercise machines). In some embodiments, a history of association may be used to infer what device should be peered with, e.g. by inferring from a user's motions that the user is done with a first exercise machine, and automatically peering with a second exercise machine if in the past, the user had used the second exercise machine next and it is available for selection (e.g. by detecting a signal from it, or by always considering it available).

Such an exercise equipment designation may be self-contained, or may be associated with a user-input description of the exercise equipment. In some embodiments, any such designation may be augmented by the user with additional information, such as an amount of weight, incline, seat settings, and any other configurable information about the exercise being performed. When such user-input data is received, it may be stored in a non-volatile memory such as a flash memory, associated with the exercise equipment designation and/or description, for later retrieval.

In some embodiments, a confirmation on the PFD may be received of the exercise equipment to be used, for example to confirm that the user is the one using, or about to use, the machine, or to confirm which exercise equipment is to be used out of a candidate set of potential equipment, which may be presented to the user and a selection thereof may be received.

In some embodiments, a PFD may learn a user's workout from his/her historical activities, and may apply the learning to future workouts. For example, the first time a user works out, s/he may enter information into the device such as a specific exercise that s/he is performing (which may include both the identity of the exercise and parameters associated with the exercise, such as an amount of weight), which may be used to aid in detecting repetitions (e.g. via an integrated accelerometer, aided by knowing what type of movement to measure, such as strides, pushing motions with arms, etc.), calculate work performed (e.g. by including a difficulty score, which may include information such as the exercise being performed, and the weight or resistance that is applied), etc. Such information may be applied successively, and software running on the PFD may store both configuration information for each such exercise, and information regarding the exercises that are performed, including the exercises performed in the course of a workout and parameters associated with those exercises.

Subsequently, when a user initiates a workout, previously entered parameters regarding each exercise in the set of stored exercises (or stored exercises associated with the place at which the user is performing the exercise, which may be deduced by geolocation, e.g. GPS matching with a previously determined set of geocoordinates at the location at which the set of stored exercises was set up or performed) may be automatically applied to the exercises and the scoring thereof. A manual override may permit a user to specify a different exercise that is being, or will be, performed.

In some embodiments, multiple exercise sets may be stored. In some embodiments, a user may manually select the desired exercise set to initiate. In some embodiments, an exercise set may be automatically determined, for example by determining that the user typically alternates between such sets and choose the next sequence in the meta-sequence, or by inferring from the day of the week, or the number of days since the last workout, or the geolocation of the workout (e.g. by GPS, wifi triangulation, and/or cell tower triangulation) and the geolocation of previous exercise sequences.

In some embodiments, a user may edit a preexisting exercise set, e.g. by being given the option on the PFD to change the set of exercises (e.g. adding or deleting exercises), and/or by updating weight, resistance, or other parameter(s) of an exercise.

In some embodiments, a set of exercises, such as exercises that a user is known to perform, or which are available at a particular location, such as a gym, may be known, for example by prior input or by downloading a database containing data characterizing such exercises. Such exercises may correspond to exercise machines. Data may be received regarding characteristics of the performance of such exercises. Such characteristic data may include a weight, incline, etc. as described above. Such characteristic data may include a characterization of the movements that are associated with performing the exercise. For example, such a characterization of movement may include information inferred from analysis of one or more accelerometers (such as a three-axis accelerometer in a PFD) during performance of the exercise, and may include the extent of a motion, the timing of the motion, and the angle of the motion. Such characterizations may be inferred by observing a continuous, or closely succeeding in time, sequence of motions with similar characterizations. For example, on an inclined press machine, a processor within a PFD could monitor the accelerometer(s) and infer that a motion of extending the arms forward at a 20 degree upward angle for approximately two seconds until an extent of 28 inches was reached, followed by a half-second at full extension, followed by a three-second retraction, the whole of which was repeated twelve times. Similarity may be gauged based on a threshold, or on grouping based on temporal criteria. Such a characterization may be stored in persistent memory, such as flash memory, and/or synchronized via a wireless or wired connection (e.g. Bluetooth or USB) to another device, and ultimately to a remote server over the Internet.

When a user initiates an exercise sequence, it may be inferred from the motion which exercise is being performed, from among the stored characterizations of prior exercises, which may include both inferred and received data. This inference of which exercise is being performed may be coupled with previously stored parameters associated with the exercise (such as an amount of weight being used). This inferred exercise may be stored as part of a record of the workout, and may be used to update the user's score, for example as discussed below in conjunction with 207 of FIG. 2.

In some embodiments, a set of exercises, such as exercises that a user is known to perform, or which are available at a particular location, such as a gym, may be known, for example by prior input or by downloading a database containing data characterizing such exercises. Such exercises may correspond to exercise machines, e.g. a machine may have one or more exercised associated with it. Data may be received regarding characteristics of the performance of such exercises. Such characteristic data may include a weight, incline, etc. as described above. Such characteristic data may include a characterization of the location at which an exercise station, such as a machine, is located. For example, such a characterization of location may include coordinates within a location, or absolute coordinates, such as latitude, longitude, and altitude; or it may include domain-specific data, such as a relative strength of a plurality of wireless access points, such as 802.11 access points, or Bluetooth beacons, or magnetic characterizations accessible via a magnetometer. Examples of such techniques are described in Anja Bekkelien, "Bluetooth Indoor Positioning," available online from the University of Geneva; Fabio Belloni, "Bringing Navigation Indoors," available online from Nokia; Interlink Networks, "A Practical Approach to Identifying and Tracking Unauthorized 802.11 Cards and Access Points," available online from Interlink Networks; Hongyu Zhou, Hongyi Wu, Su Xia, Miao Jin, and Ning Ding, "A Distributed Triangulation Algorithm for Wireless Sensor Networks on 2D and 3D Surface," available online from the University of Louisiana at Lafayette; William Storms, "Magnetic Field Aided Indoor Navigation," available online from the Air Force Institute of Technology; and U.S. Pat. No. 7,515,578, all of which are hereby incorporated herein by reference in their entirety for all purposes. Such a characterization may be stored in persistent memory, such as flash memory, and/or synchronized via a wireless or wired connection (e.g. Bluetooth or USB) to another device, and ultimately to a remote server over the Internet.

In some embodiments, dead reckoning between exercise stations, e.g. based on accelerometer data, may be used to derive the relative locations of exercise equipment, which may be used to match relative to the location at which a previous exercise was performed. Examples are included in Michael Dippold, "Personal Dead Reckoning with Accelerometers," available online from the University of Bremen; Aaron Berk, "Dead Reckoning," available online from mbed.org; and Kurt Seifert and Oscar Camacho, "Implementing Positioning Algorithms Using Accelerometers," available online from Freescale Semiconductor, all of which are hereby incorporated by reference in their entirety for all purposes.

When a user engages in an exercise sequence, or indicates the beginning of an exercise, e.g. by tapping the phone, which may be detected as described above, a particular exercise and/or exercise equipment may be inferred from the location (either absolute or relative) at which an which exercise is being performed, from among the stored characterizations of prior exercises, which may include both inferred and received data. This inference of which exercise is being performed may be coupled with previously stored parameters associated with the exercise (such as an amount of weight being used).

This inferred exercise may be stored as part of a record of the workout, and may be used to update the user's score as discussed below.

In some embodiments, exercise equipment may be connected with (202), for example via a wireless network such as Bluetooth (including BTLE), by NFC, or by WiFi.

Parameters associated with the exercise equipment may be determined (203). One example of determining parameters is to receive the parameters from a database, or over a network, for example as discussed above. Another example of determining parameters is to communicate with the exercise equipment via a wireless network such as a Bluetooth/BTLE network and receive parameters that characterize settings such as the amount of friction applied to an exercise bike, the angle of a treadmill, the speed of a treadmill or stair climbing machine, the amount of weight being moved (for example in a weight machine), an amount of counterweight being applied (for example in an assisted pull-up/dip machine), the type of exercise and a profile thereof, etc.

In some embodiments, a PFD may receive such information and integrate it with its own information, for example by receiving an exercise type from or associated with the exercise equipment, and retrieving a weight setting.

In some embodiments, stored parameters associated with the exercise machine may be retrieved from a memory (e.g. looking it up by an identifier for the exercise machine) which may in some embodiments be done via a network, and may be transmitted to the exercise machine (204). Such parameters may be applied by the exercise machine to electronically set the resistance, such as weight, according to a resistance setting, to move the seat position according to a seat height, to move the seat back according to a seat back position, etc.

In some embodiments, the PFD may keep track of reps and/or speed (205), e.g. by use of an integrated accelerometer. In some embodiments, information regarding the specific exercise that the user is performing, whether entered immediately, received from the exercise equipment, or retrieved from storage, may be used to aid in detecting repetitions (e.g. via an integrated accelerometer, aided by knowing what type of movement to measure, such as strides, pushing motions with arms, etc.).

In some embodiments, coaching may be offered based on an analysis of the movement in combination with the exercise being performed, e.g. by detecting poor form and offering specific coaching on how to improve the form. For example, a squat may be detected to involve a relatively small amount of vertical motion in a repetition, and the user may be coached (e.g. via voice or visual display) to squat lower.

In some embodiments, a PFD may integrate other information, such as parameters as discussed above, such as the amount of work being applied, or the angle of a treadmill or the resistance of an elliptical trainer, with information regarding repetitions, to calculate an activity score for an amount of work performed, (206) which is integrated with a native scoring system on the PFD (as is known in the art and practiced by many commercially available PFD's), which in some embodiments may include translating into work units. In some embodiments, the fitness device may calculate an activity score using its own scoring of repetitions, strides, etc. and may transmit a score (or raw information about the work performed, such as exercise type, weight, and number of repetitions, and optionally timing of repetitions) to the PFD. The PFD may post-process the score or calculate a score based on the raw information provided, optionally including its own weighting or other observed activity relating to the exercise just performed.

In some embodiments, information regarding the specific exercise that the user is performing, whether entered immediately, received from the exercise equipment, or retrieved from storage, may be used to aid in calculating work performed (e.g. by including a difficulty score, which may include information such as the exercise being performed, and the weight or resistance that is applied), etc. Such information may be applied successively, and software running on the PFD may store both configuration information for each such exercise, and information regarding a sequence of exercises that are performed, including the exercises performed in the course of a workout and/or the ordering of such exercises.

An activity score may be stored, and may be displayed and/or used in overall fitness program analysis (207). For example, activity scores may be compared to thresholds and/or communicated to users as an accumulating score, a final score, and/or an indication of whether a threshold was reached. In some embodiments, advice and/or coaching may be provided based on such activity scores and/or overall fitness program analysis. For example, a suggestion may be made to increase resistance/weight based on a large number of repetitions being detected, or decrease based on a small number of repetitions being detected.

In some embodiments, an activity score and/or an indication that a threshold was reached may be transmitted to a social media service such as Facebook, via APIs that may enable subsequent display of the score and/or threshold reaching via the social media service.

Figure 3:
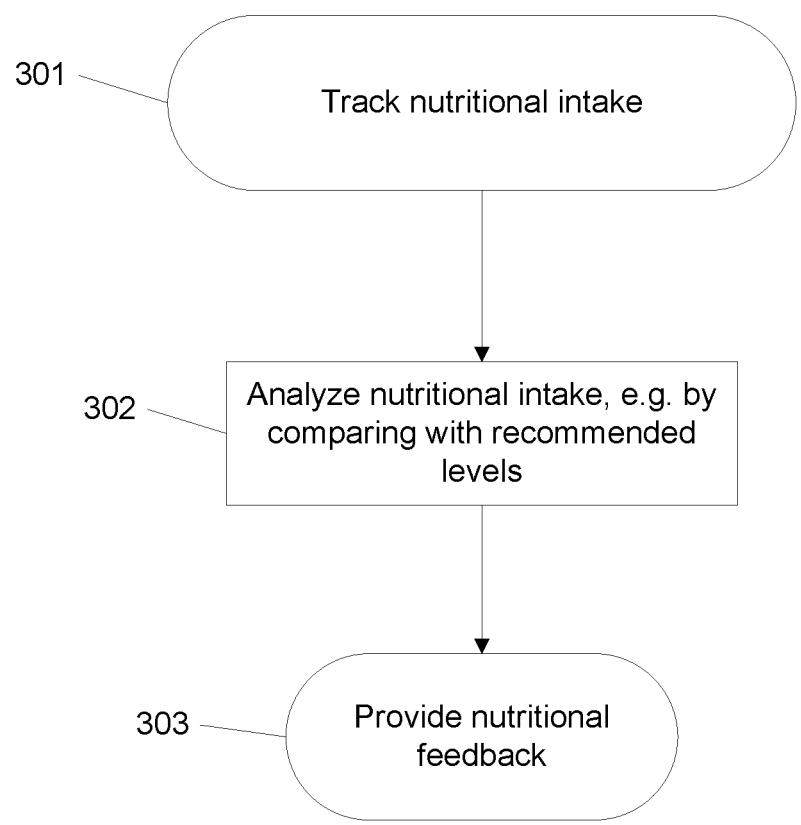
FIG. 3 is a flow diagram of a method for nutritional tracking, according to some embodiments.

FIG. 3 is a flow diagram of a method for nutritional tracking, according to some embodiments. In this example, nutritional intake is tracked (301). Nutritional intake may include calorie counts, and/or counts of individual nutrition components such as sugar, carbs, protein, portions according to the food classifications propounded by the US Department of Agriculture such as a "food pyramid" or the "MyPlate nutrition guide" (both of which are available from the USDA and are included herein by reference for all purposes), individual vitamins and minerals, etc. Such intake levels may be set as part of an overall fitness or wellness program, or as part of a weight loss program which includes caloric or nutritional requirements such as low carbohydrates, etc. In various embodiments, tracking may be performed via various means, including:

Integration with a digital wallet, either running on the same device or on a device that may be affiliated with, for example on a smartphone that a personal fitness device may connect to using Bluetooth. Such integration may take the form of receiving information relating to a purchase, including a place of purchase, and then (1) in the event such information includes SKU-level information, i.e. information about the particular items purchased, the nutritional/caloric information for the item(s) purchased may be added to running totals. If there are multiple items purchased, then a selection may be offered to the user to select which item(s) were consumed by the user (some items may have been purchased for someone else's consumption); (2) in the event such information does not include SKU-level information, the place at which a purchase was made and/or the amount of the purchase may be used to look up in a database (including via a networked call to a remote server) what candidate items may have been purchased. Such candidate items may then be presented to the user, who may select which item(s) s/he consumed. Other user interfaces, such as a user entering the name of an item and showing candidates dynamically which match the partial input, may readily be seen. The nutritional/caloric information for selected item(s) may then be used as described above.

Integration with point-of-sale (POS) systems. This is performed as in the case above, except that information is received either directly from a POS (e.g. via Bluetooth or NFC or WiFi), or indirectly from communication with a server associated with the vendor from whom a purchase has been made. Such communication may also include an intermediate server associated with the tracking service, which communicates with the device associated with the user.

Integration with credit cards or other payment instruments. In these examples, activity at a credit card network, acquiring bank, issuing bank, or other institution with knowledge of transactions, is monitored and activity matching criteria such as a credit card number associated with the user, optionally also filtered for a food vendor, is detected and sent from the financial institution to the user's device, in some embodiments using a server associated with the tracking service, which communicates with the device associated with the user. Such information may or may not include "level two" SKU-level data. After receiving transactional data, processing is performed as in the first case.

Use of geolocation and/or presence-detecting technology to determine one or more candidate locations that a user may be with. An explicit user "check-in" may also be used, guided or not by geolocation technology. For example, a user may be near three different restaurants (e.g. within a threshold, or with a centerpoint provided by the GPS within a threshold when an accuracy metric also provided by the GPS is added to the threshold to compensate for the approximacy of the location), but the GPS signal may be insufficiently accurate to know which one. All three may be presented to the user, and the user may select which one, if any, s/he is at, and then the process may continue as described in subcase (2) of the first case above.

Visual analysis of a picture taken with a camera integrated into a portable computing device, which in some embodiments may be correlated to available menu items using image recognition techniques known to those skilled in the art;

Scanning of barcodes such as UPC or QR codes, corresponding to menu items which may be looked up in a database or via a network connection.

Nutritional intake may be analyzed (302), for example by comparing caloric or nutritional information with recommended levels or other thresholds. In some embodiments, such thresholds may be dynamic, e.g. based on how much exercise has been performed or is planned to be performed. Additionally, such information may be used to alter thresholds for a subsequent meal, day, or week, for example compensating for a high-calorie meal or day with a subsequent reduction in caloric thresholds for subsequent meal(s).

Nutritional feedback may be provided (303), for example by displaying or transmitting information as to how much has been consumed and/or how much still should be consumed. In some embodiments, an overall wellness score may be computed and provided (for example, including exercise that has been performed). In some embodiments, alerts about exceeding thresholds (such as a caloric threshold or a carbohydrate threshold) or about deficiencies relative to thresholds (such as not getting enough protein, whole grains, fiber, etc.) may be provided.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method performed on a computing device, said computing device comprising at least one microprocessor coupled to at least one memory, comprising executing instructions on the at least one microprocessor for:
analyzing motion data from at least one accelerometer;
determining an exercise, wherein determining the exercise includes matching the motion data to a characteristic data, wherein the characteristic data includes a characterization of movements that are associated with performing the exercise, wherein the characterization of movements that are associated with performing the exercise is stored among a plurality of characteristic data corresponding to a plurality of exercises;
wherein determining the exercise further comprises analyzing a location of the computing device, and comparing with a known location of the exercise;
determining a parameter associated with the exercise;
detecting a number of repetitions of the exercise, wherein detecting the number of repetitions of the exercise includes analyzing second motion data from the at least one accelerometer;
calculating an activity score based at least in part on the exercise, the parameter associated with the exercise, and the number of repetitions of the exercise; and
providing the activity score.

2. The method of claim 1, wherein determining the exercise further comprises analyzing historical exercise activity.

3. The method of claim 1, wherein determining the parameter associated with the exercise equipment includes retrieving data associated with the exercise.

4. The method of claim 1, further comprising connecting to exercise equipment via a wireless network, and wherein receiving the parameter associated with the exercise includes receiving the parameter via the wireless network.

5. The method of claim 1, wherein the parameter associated with the exercise characterizes a resistance setting.

6. The method of claim 1, wherein providing the activity score includes displaying the activity score.

7. The method of claim 1, wherein providing the activity score includes incorporating the activity score into a second score associated with fitness.

8. The method of claim 1, further comprising providing coaching based at least in part on the activity score.

9. The method of claim 1, further comprising transmitting information relating to the activity score to a social media service.

10. A system, comprising:
at least one microprocessor configured to:
analyze motion data from at least one accelerometer;
determine an exercise, wherein determining the exercise includes matching the motion data to a characteristic data, wherein the characteristic data includes a characterization of movements that are associated with performing the exercise, wherein the characterization of movements that are associated with performing the exercise is stored among a plurality of characteristic data corresponding to a plurality of exercises;
wherein determining the exercise further comprises analyzing a location of the computing device, and comparing with a known location of the exercise;
determine a parameter associated with the exercise;
detect a number of repetitions of the exercise, wherein detecting the number of repetitions of the exercise includes analyzing second motion data from the at least one accelerometer;
calculate an activity score based at least in part on the exercise, the parameter associated with the exercise, and the number of repetitions of the exercise; and
provide the activity score; and at least one memory coupled with the at least one microprocessor, wherein the at least one memory provides instructions to the at least one microprocessor.

11. The system of claim 10, wherein determining the exercise includes analyzing historical exercise activity.

12. A computer program product, the computer program product being embodied in a non-transitory computer readable medium and comprising computer instructions for:
analyzing motion data from at least one accelerometer;
determining an exercise, wherein determining the exercise includes matching the motion data to a characteristic data, wherein the characteristic data includes a characterization of movements that are associated with performing the exercise, wherein the characterization of movements that are associated with performing the exercise is stored among a plurality of characteristic data corresponding to a plurality of exercises;
wherein determining the exercise further comprises analyzing a location of the computing device, and comparing with a known location of the exercise;
determining a parameter associated with the exercise;
detecting a number of repetitions of the exercise, wherein detecting the number of repetitions of the exercise includes analyzing second motion data from the at least one accelerometer;
calculating an activity score based at least in part on the exercise, the parameter associated with the exercise, and the number of repetitions of the exercise; and
providing the activity score.

13. The computer program product of claim 12, wherein determining the exercise equipment includes analyzing historical exercise activity.

14. The method of claim 1, wherein the motion data includes an extent of a motion.

15. The method of claim 1, wherein the motion data includes an timing of a motion.

16. The method of claim 1, wherein the motion data includes an angle of a motion.

17. The method of claim 1, wherein the parameter associated with the exercise includes an amount of weight.

18. The system of claim 10, wherein determining the exercise further comprises analyzing historical exercise activity.

19. The computer program product of claim 12, wherein determining the exercise further comprises analyzing historical exercise activity.

* * * * *